(12) United States Patent
Hu et al.

(10) Patent No.: US 12,391,707 B2
(45) Date of Patent: Aug. 19, 2025

(54) PREPARATION METHOD FOR OXAZEPINE COMPOUND

(71) Applicant: FUJIAN AKEYLINK BIOTECHNOLOGY CO., LTD., Ningde (CN)

(72) Inventors: Yanbin Hu, Shanghai (CN); Fei Sun, Shanghai (CN); Charles Z. Ding, Shanghai (CN)

(73) Assignee: FUJIAN AKEYLINK BIOTECHNOLOGY CO., LTD., Ningde (CN)

( * ) Notice: Subject to any disclaimer, the term of this patent is extended or adjusted under 35 U.S.C. 154(b) by 847 days.

(21) Appl. No.: 17/635,462

(22) PCT Filed: Jul. 28, 2020

(86) PCT No.: PCT/CN2020/105248
§ 371 (c)(1),
(2) Date: Feb. 15, 2022

(87) PCT Pub. No.: WO2021/027566
PCT Pub. Date: Feb. 18, 2021

(65) Prior Publication Data
US 2022/0306648 A1 Sep. 29, 2022

(30) Foreign Application Priority Data
Aug. 15, 2019 (CN) .......................... 201910754972.2

(51) Int. Cl.
*C07D 498/04* (2006.01)

(52) U.S. Cl.
CPC ................................. *C07D 498/04* (2013.01)

(58) Field of Classification Search
CPC .................................................. C07D 498/04
USPC ...................................................... 540/551
See application file for complete search history.

(56) References Cited

FOREIGN PATENT DOCUMENTS

| | | |
|---|---|---|
| CN | 107849037 A | 3/2018 |
| CN | 108884107 A | 11/2018 |
| CN | 109715624 A | 5/2019 |
| CN | 110114071 A | 8/2019 |
| JP | 2015522034 A | 8/2015 |
| JP | 2018522864 A | 8/2018 |
| WO | 2014005129 A1 | 1/2014 |
| WO | 2016210215 A1 | 12/2016 |
| WO | 2017013046 A1 | 1/2017 |
| WO | 2018022282 A1 | 2/2018 |
| WO | 2018085619 A1 | 5/2018 |
| WO | 2018214875 A1 | 11/2018 |
| WO | 20200197409 A1 | 6/2020 |

OTHER PUBLICATIONS

Oct. 3, 2023 Second Notice of Reasons for Refusal issued in Japanese Patent Application No. 2022-509613.
Office Action for Chinese Patent Application No. 2020107372852, mailed Jan. 19, 2023.
Pouyan Haghshenas et al., "Chemo- and Diastereoselective N-Heterocyclic Carbene-Catalyzed Cross-Benzoin Reactions Using N-Boc-α-amino Aldehydes," Organic Letters, Aug. 30, 2016.
International Search Report issued in International Patent Application No. PCT/CN2020/105248, mailed Oct. 28, 2020.
Written Opinion of the International Searching Authority issued in International Patent Application No. PCT/CN2020/105248, mailed Oct. 28, 2020.
Harry L a Janssen et al., "Pegylated interferon alfa-2b alone or in combination with lamivudine for HBeAg-positive chronic hepatitis B: a randomised trial," Jan. 8, 2005, pp. 123-129, vol. 365.
Patrick Marcellin et al, "Peginterferon Alfa-2a Alone, Lamivudine Alone, and the Two in Combination in Patients with HBeAg-Negative Chronic Hepatitis B," N. Engl. J. Med., Sep. 2004, pp. 1,206-1,217, vol. 351, No. 12.
Erik H. C. J. Buster et al., "Peginterferon Alpha-2b Is Safe and Effective in HBeAg-Positive Chronic Hepatitis B Patients with Advanced Fibrosis," Hepatology, Aug. 2007, pp. 388-394, 46.
Theodora W. Greene et al., "Protective Groups in Organic Synthesis," Wiley and Sons, 1991.
Nov. 3, 2022, First Office Action issued in Chinese Patent Application No. 2020107372852.
Notice of Reasons for Refusal issued in Japanese Patent Application No. 2022-509613, mailed May 30, 2023.

*Primary Examiner* — Kristin A Vajda
(74) *Attorney, Agent, or Firm* — Pilloff Passino & Cosenza LLP; Rachel K. Pilloff; Sean A. Passino

(57) ABSTRACT

Provided is a preparation method for an oxazepine compound, and specifically disclosed are a preparation method for a compound of formula (I) and an intermediate of same.

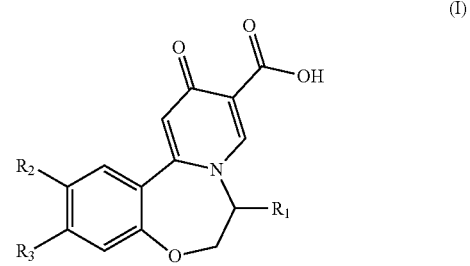

(I)

17 Claims, No Drawings

PREPARATION METHOD FOR OXAZEPINE COMPOUND

The present application claims priority to Chinese Patent Application No. 201910754972.2 filed on Aug. 15, 2019, the contents of which are incorporated herein by reference in their entireties.

TECHNICAL FIELD

The present disclosure relates to a preparation method for oxazepine compounds.

BACKGROUND

Viral hepatitis B, shortened to hepatitis B, is a disease caused by the infection of the body with the hepatitis B virus (HBV). The hepatitis B virus is a hepatotropic virus, and is mainly present in hepatocytes and damages hepatocytes, causing inflammation, necrosis and fibrosis of hepatocytes. Viral hepatitis B is classified into acute and chronic types. Acute hepatitis B will mostly clear up of its own accord in adults due to their own immune mechanisms. However, chronic hepatitis B (CHB) has become a great challenge for health care worldwide, and is also a major cause of chronic liver diseases, cirrhosis and hepatocellular carcinoma (HCC). It is estimated that 2 billion people worldwide are infected with the chronic hepatitis B virus, more than 350 million people have developed hepatitis B, and nearly 600 thousand people each year die from complications of chronic hepatitis B. China is a high-incidence area of hepatitis B, and there are many accumulated patients with hepatitis B, causing serious harm. According to the data, there are about 93 million people infected with the hepatitis B virus in China at present, among which about 20 million patients are diagnosed with chronic hepatitis B; the disease in 10%-20% of the patients may develop into cirrhosis, and that in 1%-5% of the patients may develop into liver cancer.

The key to the functional cure of hepatitis B is the clearance of HBsAg (the surface antigen of the hepatitis B virus) and the production of surface antibodies. HBsAg quantification is a very important bioindicator. In chronically infected patients, a reduction in HBsAg and seroconversion, endpoints of the current therapy, are rarely observed.

Patent application WO2018214875 found a surface antigen inhibitor capable of effectively reducing HBsAg. Currently approved anti-HBV drugs on the market are mainly immunomodulators (interferon-α and peginterferon-α-2α) and antiviral therapeutic drugs (lamivudine, adefovir dipivoxil, entecavir, telbivudine, tenofovir, clevudine, etc.). Among them, the antiviral therapeutic drugs belong to nucleotide drugs, and their action mechanism is to inhibit the synthesis of HBV DNA rather than to reduce the HBsAg level directly. As with the extended therapy, the nucleotide drugs show HBsAg clearance rates similar to those observed in nature (Janssen et al. *Lancet* (2005), 365, 123-129; Marcellin et al. *N. Engl. J. Med.* (2004), 351, 1206-1217; Buster et al. *Hepatology* (2007), 46, 388-394). The existing clinical therapies have poor therapeutic effects in reducing HBsAg. Therefore, there is an urgent need for the development of a small-molecule oral inhibitor capable of effectively reducing HBsAg for clinical administration at present. In order to further study the effectiveness and safety of the molecule in treating hepatitis B, the process for large-scale production is studied, and its structure is shown below:

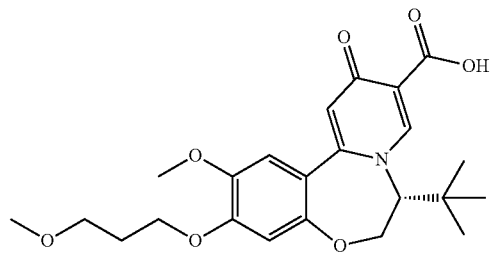

CONTENT OF THE PRESENT INVENTION

The present disclosure provides a preparation method for a compound of formula (I),

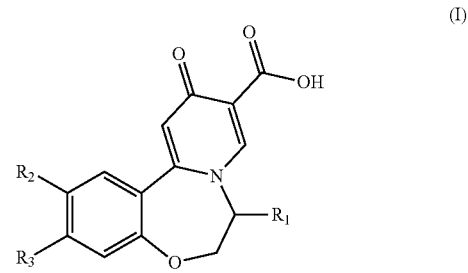

which comprises the following steps:

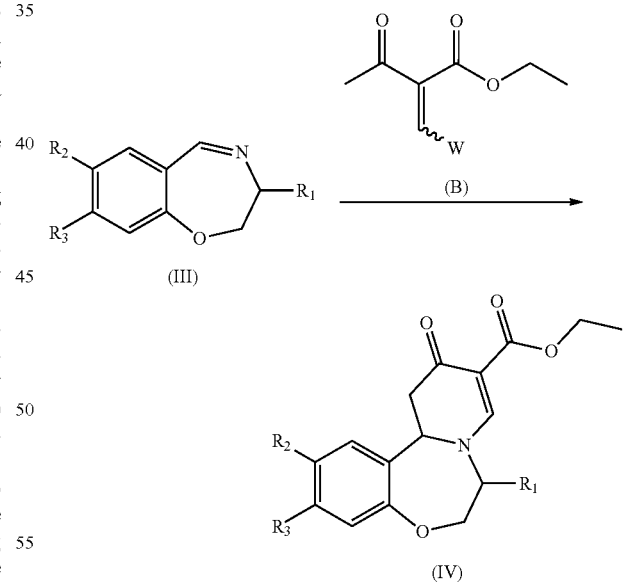

wherein,

W is selected from OH, $C_{1-6}$ alkoxy and $C_{1-6}$ alkylamino;

$R_1$ is selected from $C_{1-6}$ alkyl;

$R_2$ is selected from H, F, Cl, Br, I, CN, $C_{1-6}$ alkyl, $C_{1-6}$ alkoxy, $C_{1-6}$ alkylamino, —C(=O)—$C_{1-6}$ alkyl, $C_{3-6}$ cycloalkyl and 3-6 membered heterocycloalkyl, wherein the $C_{1-6}$ alkyl, $C_{1-6}$ alkoxy, $C_{1-6}$ alkylamino, $C_{3-6}$ cycloalkyl and 3-6 membered heterocycloalkyl are optionally substituted with 1, 2 or 3 $R_a$;

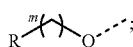

R₃ is selected from

R is selected from H, OH, CN, NH₂, $C_{1-6}$ alkyl, $C_{1-6}$ alkoxy, $C_{1-6}$ alkylamino, $C_{1-6}$ alkylthio, —C(=O)—$C_{1-6}$ alkyl, —C(=O)—$C_{1-6}$ alkylamino, —O—C(=O)—$C_{1-6}$ alkylamino, —NH—C(=O)—$C_{1-6}$ alkoxy, $C_{2-5}$ alkenyl, $C_{2-5}$ heteroalkenyl, $C_{3-6}$ cycloalkyl and 3-6 membered heterocycloalkyl, wherein the $C_{1-6}$ alkyl, $C_{1-6}$ alkoxy, $C_{1-6}$ alkylamino, $C_{1-6}$ alkylthio, —C(=O)—$C_{1-6}$ alkyl, —C(=O)—$C_{1-6}$ alkylamino, —O—C(=O)—$C_{1-6}$ alkylamino, —NH—C(=O)—$C_{1-6}$ alkoxy, $C_{2-5}$ alkenyl, $C_{2-5}$ heteroalkenyl, $C_{3-6}$ cycloalkyl and 3-6 membered heterocycloalkyl are optionally substituted with 1, 2 or 3 $R_b$;

m is selected from 0, 1, 2, 3, 4 and 5;

$R_a$ and $R_b$ are each independently selected from COOH, F, Cl, Br, I, OH, CN, NH₂, CH₃, CH₂CH₃, CH₂CH₂CH₃, OCH₃, —NHCH₃, —N(CH₃)₂ and CF₃.

In some embodiments of the present disclosure, R is selected from H, OH, CN, NH₂, $C_{1-3}$ alkyl, $C_{1-3}$ alkoxy, $C_{1-3}$ alkylamino, $C_{1-3}$ alkylthio, —C(=O)—$C_{1-3}$ alkyl, —C(=O)—$C_{1-3}$ alkylamino, —O—C(=O)—$C_{1-3}$ alkylamino, —NH—C(=O)—$C_{1-3}$ alkoxy, $C_{2-3}$ alkenyl, $C_{2-3}$ heteroalkenyl, $C_{3-6}$ cycloalkyl and 3-6 membered heterocycloalkyl, wherein the $C_{1-3}$ alkyl, $C_1$-3 alkoxy, $C_{1-3}$ alkylamino, $C_{1-3}$ alkylthio, —C(=O)—$C_{1-3}$ alkyl, —C(=O)—$C_{1-3}$ alkylamino, —O—C(=O)—$C_{1-3}$ alkylamino, —NH—C(=O)—$C_{1-3}$ alkoxy, $C_{2-3}$ alkenyl, $C_{2-3}$ heteroalkenyl, $C_{3-6}$ cycloalkyl and 3-6 membered heterocycloalkyl are optionally substituted with 1, 2 or 3 $R_b$.

In some embodiments of the present disclosure, R is selected from H, OH, CN, NH₂,

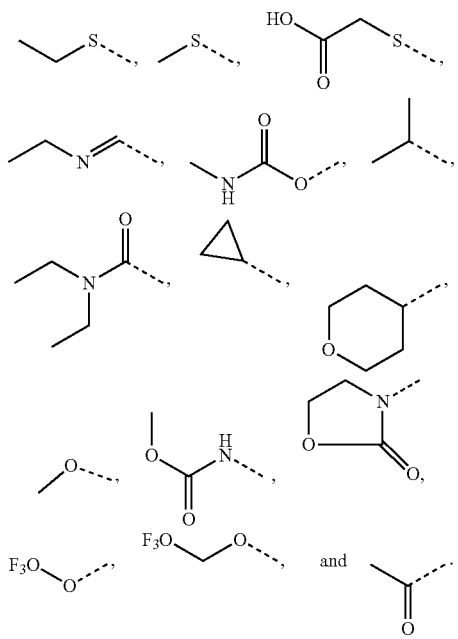

In some embodiments of the present disclosure, W is selected from OH, —OCH₂CH₃ and —N(CH₃)₂.

In some embodiments of the present disclosure, $R_1$ is selected from

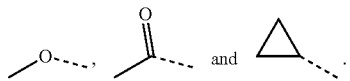

In some embodiments of the present disclosure, $R^2$ is selected from H, F, Cl, Br, I, CN, $C_{1-3}$ alkyl, $C_{1-3}$ alkoxy, $C_{1-3}$ alkylamino, —C(=O)—$C_{1-3}$ alkyl, $C_{3-6}$ cycloalkyl and 3-6 membered heterocycloalkyl, wherein the $C_{1-3}$ alkyl, $C_{1-3}$ alkoxy, $C_{1-3}$ alkylamino, —C(=O)—$C_{1-3}$ alkyl, $C_{3-6}$ cycloalkyl and 3-6 membered heterocycloalkyl are optionally substituted with 1, 2 or 3 $R_a$.

In some embodiments of the present disclosure, $R_2$ is selected from Cl, Br, CN, CH₃,

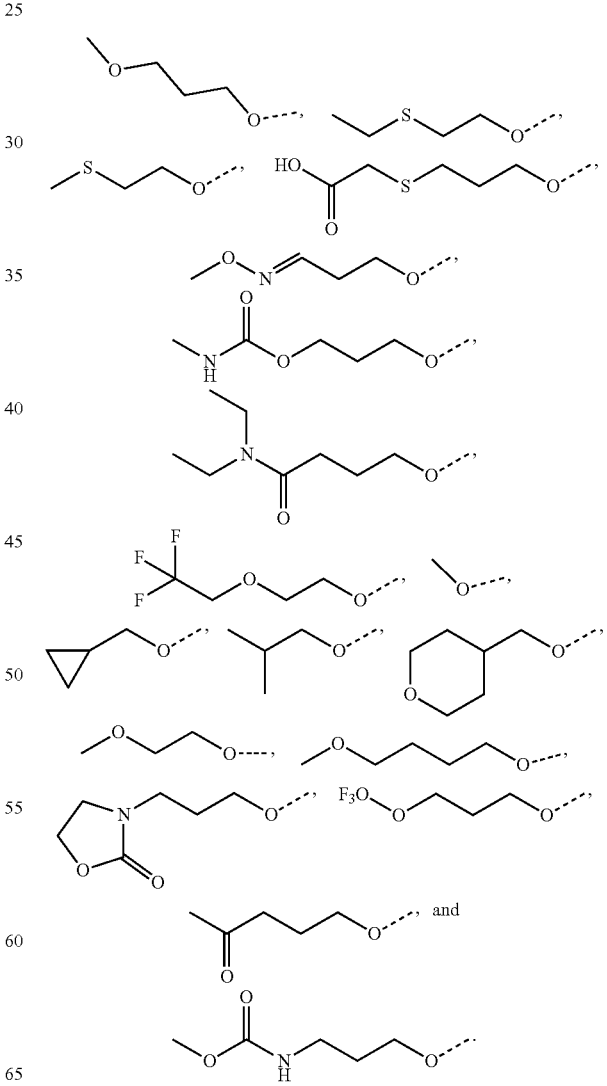

In some embodiments of the present disclosure, the preparation method described above comprises the following steps:

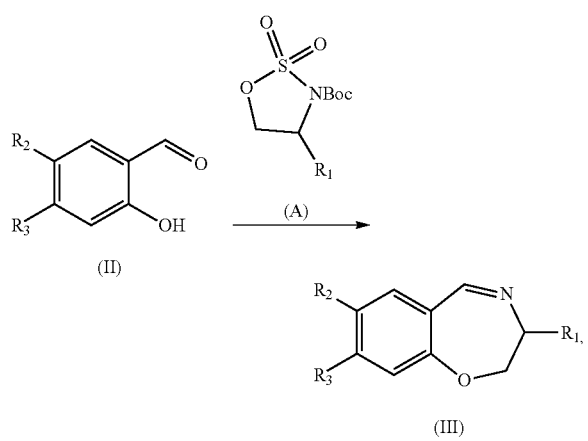

wherein $R_1$, $R_2$ and $R_3$ are defined as in the present disclosure.

In some embodiments of the present disclosure, the preparation method described above comprises the following steps:

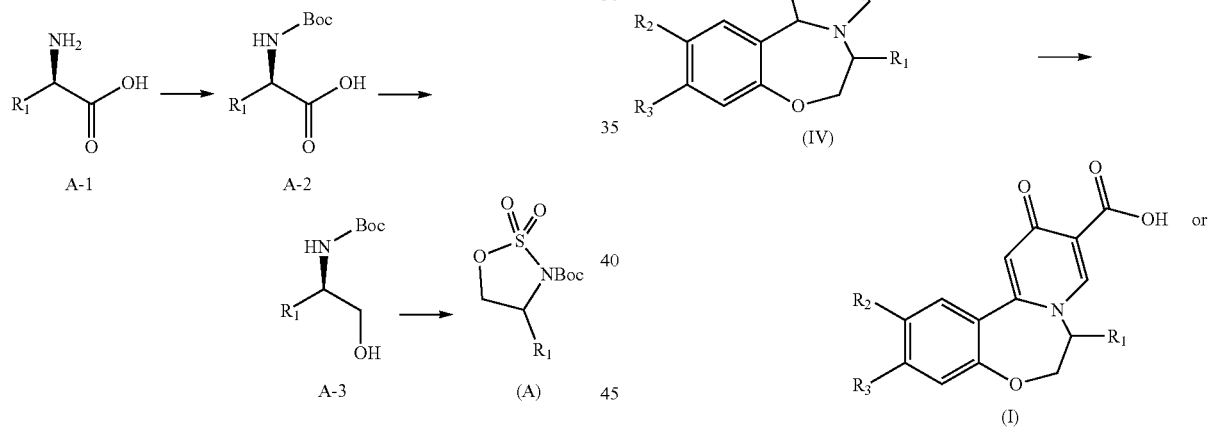

wherein $R_1$ is defined as in the present disclosure.

In some embodiments of the present disclosure, the preparation method described above comprises the following steps:

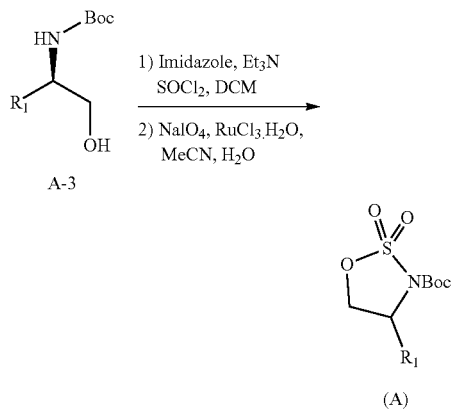

wherein $R_1$ is defined as in the present disclosure.

In some embodiments of the present disclosure, the preparation method described above comprises the following steps:

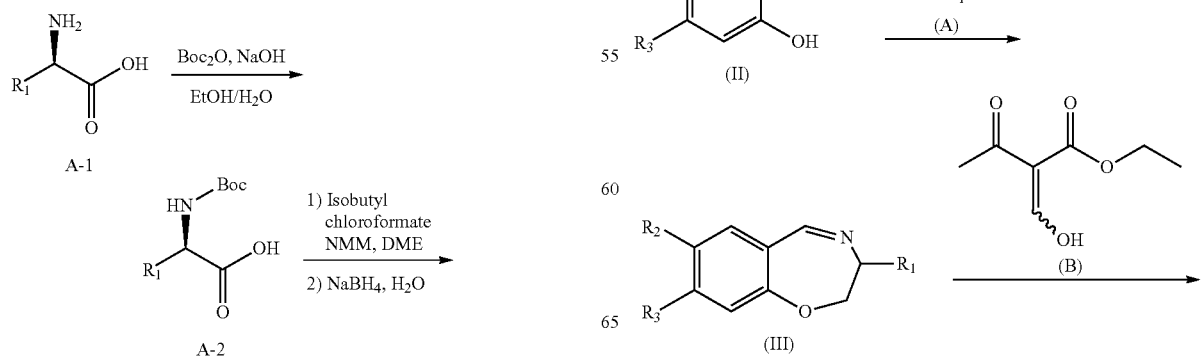

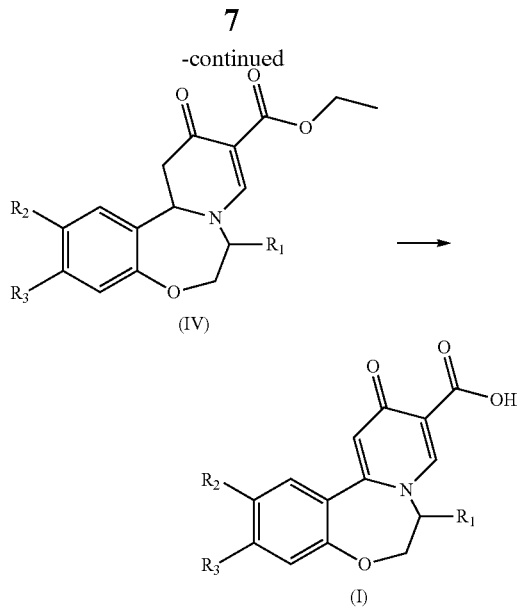

wherein $R_1$, $R_2$ and $R_3$ are defined as in the present disclosure.

TECHNICAL EFFECTS

In the medicinal chemistry patent application (WO2018214875), when compound IV is synthesized by cyclization, the starting materials used are compound III and compound B-1, and compound B-1 has a structure as shown below:

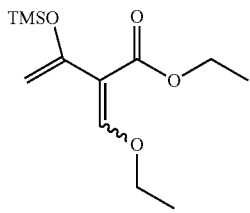

The reaction has poor repeatability and low yield, with only about 7% yield of compound 3 in the medicinal chemistry synthesis process. The compound B-1 for cyclization requires harsh synthesis conditions, and is difficult to purify. In addition, the purity of compound B-1 is uncontrollable, leading to low yield in the subsequent cyclization reaction and poor repeatability. When compound B is used for reaction, firstly, the reagent is easy to prepare, the method is economical and environment-friendly, and the quality is controllable. Moreover, the yield is greatly improved (80%) by adopting compound B, and the reaction is stable and can be employed in scale-up production.

Secondly, compound III is obtained subsequently to the alkylation of compound (II) and compound (A). The advantage of the method is that excellent reaction results with high yield can be achieved even when $R_1$ has large steric hindrance (e.g., $R_1$=tert-butyl).

Thirdly, for the synthesis of compound A-3, after optimization and screening of the process in the present disclosure, compound A-3 can be stably and safely produced on a large scale by utilizing the reaction of isobutyl chloroformate with carboxylic acid to generate active ester and then the reduction of carboxylic acid by the milder reducing agent sodium borohydride to obtain the desired hydroxyl group. Carboxylic acid can be reduced into hydroxyl by several methods, e.g., by direct reduction by lithium aluminum hydride, by direct reduction by a solution of borane-tetrahydrofuran, or by esterification of carboxylic acid followed by reduction by milder reducing agent such as lithium borohydride, sodium borohydride, or potassium borohydride.

After optimization and screening of the process, the advantages of the present disclosure are mainly as follows:

1. Sodium borohydride is less expensive than lithium aluminum hydride.

2. Lithium aluminum is chemically active relative to sodium borohydride, and is a safety hazard as it is highly susceptible to spontaneous combustion when exposed to water or moist air, not favoring scale-up production.

3. The active ester obtained by sodium borohydride reduction is stable compared to that obtained by lithium aluminum hydride. Sodium borohydride is added at about 0° C., which is an appropriate temperature for scale-up production with low energy consumption.

Definitions and Description

Unless otherwise stated, the following terms and phrases used herein are intended to have the following meanings. A particular phrase or term, unless otherwise specifically defined, should not be considered as uncertain or unclear, but construed according to its common meaning. When referring to a trade name, it is intended to refer to its corresponding commercial product or its active ingredient.

The intermediate compounds of the present disclosure can be prepared by a variety of synthetic methods well known to those skilled in the art, including the specific embodiments listed below, embodiments formed by combinations thereof with other chemical synthetic methods, and equivalent substitutions thereof known to those skilled in the art. Preferred embodiments include, but are not limited to, the examples of the present disclosure.

The chemical reactions of the specific embodiments of the present disclosure are carried out in a suitable solvent that must be suitable for the chemical changes in the present disclosure and the reagents and materials required. In order to obtain the compounds of the present disclosure, it is sometimes necessary for those skilled in the art to modify or select a synthesis procedure or a reaction scheme based on the existing embodiments.

An important consideration in any synthesis route planning in the art is the selection of suitable protecting groups for reactive functional groups (e.g., the amino group in the present disclosure). *Protective Groups In Organic Synthesis* (Wiley and Sons, 1991) by Greene and Wuts is an authority for trained practitioners in this regard. All references cited in the present disclosure are incorporated in the present disclosure in their entirety.

"Optional" or "optionally" means that the subsequently described event or circumstance may, but does not necessarily, occur, and the description includes instances where the event or circumstance occurs and instances where it does not.

The term "substituted" means that one or more hydrogen atoms on a specific atom are substituted with substituents which may include deuterium and hydrogen variants, as long as the valence of the specific atom is normal and the substituted compound is stable. When the substituent is an oxygen (i.e., =O), it means that two hydrogen atoms are substituted. Substitution with oxygen does not occur on aromatic groups. The term "optionally substituted" means that an atom can be substituted with a substituent or not. Unless otherwise specified, the type and number of the substituent may be arbitrary as long as being chemically achievable.

When any variable (e.g., R) occurs more than once in the constitution or structure of a compound, the variable is independently defined in each case. Thus, for example, if a group is substituted with 0-2 R, the group can be optionally substituted with up to two R, and the definition of R in each case is independent. Furthermore, a combination of a substituent and/or a variant thereof is permissible only if the combination can result in a stable compound.

When the number of a linking group is 0, for example, —(CRR)$_0$—, it means that the linking group is a single bond.

When the number of a substituent is 0, it means that there is no such a substituent in a structure. For example, -A-(R)$_0$ means that the structure is actually -A.

When a substituent is absent, it means that there is no such a substituent in a structure. For example, when X is absent in A-X, it means that the structure is actually A.

When one of variables is selected from a single bond, it means that the two groups are linked directly. For example, in A-L-Z, when L represents a single bond, it means that the structure is actually A-Z.

Unless otherwise specified, the number of atoms in a ring is generally defined as the member number of the ring. For example, "5-7 membered ring" refers to a "ring" in which 5 to 7 atoms are arranged in a circle.

Unless otherwise specified, the term "$C_{1-6}$ alkyl" refers to a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl and the like, and may be monovalent (e.g., methyl), divalent (e.g., methylene), or polyvalent (e.g., methenyl). Examples of $C_{1-6}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, etc.

Unless otherwise specified, the term "$C_{1-3}$ alkyl" refers to a linear or branched saturated hydrocarbon group consisting of 1 to 3 carbon atoms. The $C_{1-3}$ alkyl includes, but is not limited to, $C_{1-2}$ and $C_{2-3}$ alkyl and the like, and may be monovalent (e.g., methyl), divalent (e.g., methylene), or polyvalent (e.g., methenyl). Examples of $C_{1-3}$ alkyl include, but are not limited to, methyl (Me), ethyl (Et), propyl (including n-propyl and isopropyl), etc.

Unless otherwise specified, the term "$C_{1-6}$ alkoxy" refers to those alkyl groups that each contains 1 to 6 carbon atoms and is linked to the rest part of the molecule through an oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$ and $C_3$ alkoxy and the like. Examples of $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentyloxy (including n-pentyloxy, isopentyloxy and neopentyloxy), hexyloxy, etc.

Unless otherwise specified, the term "$C_{1-3}$ alkoxy" refers to those alkyl groups that each contains 1 to 3 carbon atoms and is linked to the rest part of the molecule through an oxygen atom. The $C_{1-3}$ alkoxy includes $C_{1-2}$, $C_{2-3}$, $C_3$ and $C_2$ alkoxy and the like. Examples of $C_{1-3}$ alkoxy include, but are not limited to, methoxy, ethoxy, propoxy (including n-propoxy and isopropoxy), etc.

Unless otherwise specified, the term "$C_{1-6}$ alkylamino" refers to those alkyl groups that each contains 1 to 6 carbon atoms and is linked to the rest part of the molecule through an amino group. The $C_{1-6}$ alkylamino includes $C_{1-4}$, $C_{1-3}$, $C_{1-2}$, $C_{2-6}$, $C_{2-4}$, $C_6$, $C_5$, $C_4$, $C_3$ and $C_2$ alkylamino and the like. Examples of $C_{1-6}$ alkylamino include, but are not limited to, —NHCH$_3$, —N(CH$_3$)$_2$, —NHCH$_2$CH$_3$, —N(CH$_3$)CH$_2$CH$_3$, —N(CH$_2$CH$_3$)(CH$_2$CH$_3$), —NHCH$_2$CH$_2$CH$_3$, —NHCH$_2$(CH$_3$)$_2$, —NHCH$_2$CH$_2$CH$_2$CH$_3$, etc.

Unless otherwise specified, the term "$C_{1-3}$ alkylamino" refers to those alkyl groups that each contains 1 to 3 carbon atoms and is linked to the rest part of the molecule through an amino group. The $C_{1-3}$ alkylamino includes $C_{1-2}$, $C_3$ and $C_2$ alkylamino and the like. Examples of $C_{1-3}$ alkylamino include, but are not limited to, —NHCH$_3$, —N(CH$_3$)$_2$, —NHCH$_2$CH$_3$, —N(CH$_3$)CH$_2$CH$_3$, —NHCH$_2$CH$_2$CH$_3$, —NHCH$_2$(CH$_3$)$_2$, etc.

Unless otherwise specified, the term "$C_{1-6}$ alkylthio" refers to those alkyl groups that each contains 1 to 6 carbon atoms and is linked to the rest part of the molecule through a sulfur atom. The $C_{1-6}$ alkylthio includes $C_{1-4}$, $C_{1-3}$, $C_{1-2}$, $C_{2-6}$, $C_{2-4}$, $C_6$, $C_5$, $C_4$, $C_3$ and $C_2$ alkylthio and the like. Examples of $C_{1-6}$ alkylthio include, but are not limited to, —SCH$_3$, —SCH$_2$CH$_3$, —SCH$_2$CH$_2$CH$_3$, —SCH$_2$(CH$_3$)$_2$, etc.

Unless otherwise specified, the term "$C_{1-3}$ alkylthio" refers to those alkyl groups that each contains 1 to 3 carbon atoms and is linked to the rest part of the molecule through a sulfur atom. The $C_{1-3}$ alkylthio includes $C_{1-3}$, $C_{1-2}$ and $C_3$ alkylthio and the like. Examples of $C_{1-3}$ alkylthio include, but are not limited to, —SCH$_3$, —SCH$_2$CH$_3$, —SCH$_2$CH$_2$CH$_3$, —SCH$_2$(CH$_3$)$_2$, etc.

Unless otherwise specified, the term "heteroalkenyl", by itself or in combination with another term, refers to a stable linear or branched alkenyl radical or a combination thereof consisting of a specified number of carbon atoms and at least one heteroatom or heteroatom group. In some embodiments, the heteroatom is selected from B, O, N, and S, wherein nitrogen and sulfur atoms are optionally oxidized and the nitrogen heteroatom is optionally quaternized. In other embodiments, the heteroatom group is selected from —C(=O)O—, —C(=O)—, —C(=S)—, —S(=O), —S(=O)$_2$—, —C(=O)N(H)—, —N(H)—, —C(=NH)—, =N—, —S(=O)$_2$N(H)— and —S(=O)N(H)—. In some embodiments, the heteroalkenyl is $C_{2-5}$ heteroalkenyl; in other embodiments, the heteroalkenyl is $C_{2-3}$ heteroalkenyl. The heteroatom or heteroatom group may be located at any interior position of heteroalkenyl, including the position where the alkenyl is linked to the rest part of the molecule. However, the terms "alkenyloxy", "alkenylamino" and "alkenylthio" are commonly used expressions and refer to those alkenyl groups linked to the rest part of the molecule through an oxygen atom, an amino group, or a sulfur atom, respectively. Examples of heteroalkenyl include, but are not limited to, —O—CH=CH$_2$, —O—CH=CHCH$_3$, —O—CH=C(CH$_3$)$_2$, —CH=CHO—CH$_3$, —O—CH=CHCH$_2$CH$_3$, —CH$_2$—CH=CH—OCH$_3$, —NH—CH=CH$_2$, —N(CH=CH$_2$)—CH$_3$, —CH=CH—NH—CH$_3$, —CH=CH—N(CH$_3$)$_2$, —S—CH=CH$_2$, —S—CH=CHCH$_3$, —S—CH=C(CH$_3$)$_2$, —CH$_2$—S—CH=CH$_2$, —S(=O)—CH=CH$_2$ and —CH=CH—S(=O)$_2$—CH$_3$. At most two heteroatoms can be consecutive, e.g., —CH=CH—NH—OCH$_3$.

Unless otherwise specified, "$C_{3-6}$ cycloalkyl" refers to a saturated cyclic hydrocarbon group consisting of 3 to 6 carbon atoms, including monocyclic and bicyclic ring systems. The $C_{3-6}$ cycloalkyl includes $C_{3-5}$, $C_{4-5}$ and $C_{5-6}$ cycloalkyl and the like, and may be monovalent, divalent or polyvalent. Examples of $C_{3-6}$ cycloalkyl include, but are not limited to, cyclopropyl, cyclobutyl, cyclopentyl, cyclohexyl, etc.

Unless otherwise specified, the term "3-8 membered heterocycloalkyl", by itself or in combination with other terms, refers to a saturated cyclic group consisting of 3 to 8 ring atoms, of which 1, 2, 3, or 4 ring atoms are heteroatoms independently selected from the group consisting of O, S and N, with the remaining being carbon atoms. The nitrogen atom is optionally quaternized, and the nitrogen and sulfur heteroatoms can be optionally oxidized (i.e., NO and $S(O)_p$, where p is 1 or 2). This includes monocyclic and bicyclic systems, wherein the bicyclic system includes spirocyclic, fused, and bridged rings. Furthermore, with respect to the "3-8 membered heterocycloalkyl", a heteroatom may occupy the position where the heterocycloalkyl is linked to the rest of the molecule. The 3-8 membered heterocycloalkyl includes 3-6 membered, 3-5 membered, 4-6 membered, 5-6 membered, 4 membered, 5 membered and 6 membered heterocycloalkyl and the like. Examples of 3-8 membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl, tetrahydrothien-3-yl, etc.), tetrahydrofuryl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl, dioxepanyl, etc.

The present disclosure is described in detail below by way of examples, which are not intended to limit the present disclosure in any way.

All solvents used in the present disclosure are commercially available.

The following abbreviations are used in the present disclosure: DCM represents dichloromethane; EtOH represents ethanol; DME represents ethylene glycol dimethyl ether; MeCN represents acetonitrile; Bn represents benzyl; Boc represents tert-butylcarbonyl, an amine-protecting group; $Boc_2O$ represents di-tert-butyl dicarbonate; NMM represents N-methylmorpholine.

Compounds are named either manually or by ChemDraw® software, and supplier's catalog names are given for commercially available compounds.

DETAILED DESCRIPTION OF THE PREFERRED EMBODIMENT

In order to better understand the content of the present disclosure, further description is given with reference to specific examples, but the specific embodiments are not intended to limit the content of the present disclosure.

Example 1: Preparation of Compound 4

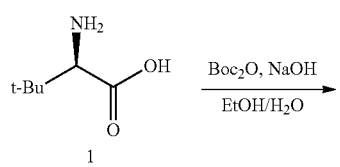

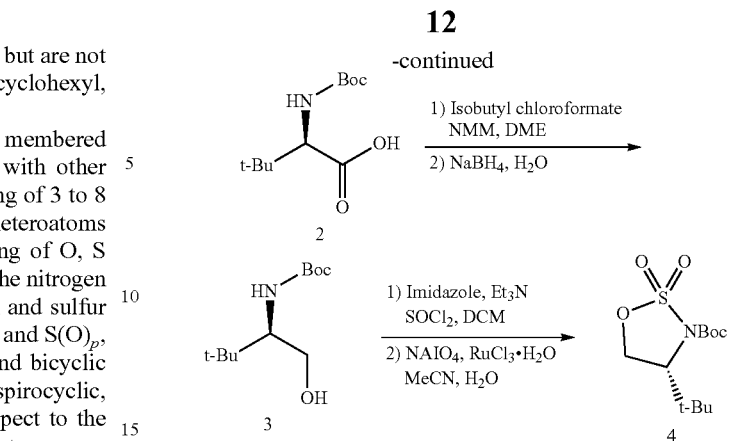

Step 1: Compound 2

Ethanol (6.0 L) and water (6.0 L) were added to a 50 L reactor at room temperature, followed by compound 1 (3000.00 g, 22.871 mol). The mixture was well mixed by stirring without dissolution. The solution of sodium hydroxide (1006.20 g, 25.155 mol) in water (6.0 L) was slowly added dropwise to the reactor over about 0.5 h at a controlled temperature of 20-30° C. $Boc_2O$ (5989.80 g, 27.445 mol) was dissolved in ethanol (3.0 L), and the resulting solution was slowly added dropwise to the reactor over about 1 h at a controlled temperature of 20-30° C. The mixture was stirred for 16 h at a controlled temperature of 25-30° C. The reaction was completed as detected by TLC. The reaction mixture was concentrated by rotary evaporation under a reduced pressure of −0.095 MPa at 50° C. to evaporate a mixture of ethanol and water (9.2 L). The concentrate was diluted with ethyl acetate (9.0 L) and adjusted to pH=3-4 with citric acid (1500.00 g) under stirring, followed by liquid separation. Ethyl acetate (9.0 L) was added for extraction, followed by liquid separation. The organic phases were combined, washed with brine (3.0 L×2), dried over anhydrous sodium sulfate (1000.00 g), and filtered. The mother liquor was collected and evaporated by rotary evaporation under a reduced pressure of −0.095 MPa at 50° C. to obtain compound 2 as a white solid (5115.23 g, 96.76% yield).

$^1$H NMR (400 MHz, CHLOROFORM-d) δ=7.05-6.27 (m, 1H), 5.92 (br s, 1H), 5.04 (br d, J=8.7 Hz, 1H), 4.05 (br d, J=9.2 Hz, 1H), 1.39-1.37 (m, 9H), 0.95 (s, 9H).

Step 2: Compound 3

To a 50 L reactor was added ethylene glycol dimethyl ether (20.0 L) at room temperature, followed by compound 2 (2515.00 g, 10.874 mol) and N-methylmorpholine (1165.88 g, 11.526 mol) under a nitrogen atmosphere. The mixture was cooled to −5° C. Isobutyl chloroformate (1559.40 g, 11.417 mol) was slowly added dropwise over about 1 h at a controlled temperature of −20-0° C., with heat released. The mixture was stirred for 16 h at a controlled temperature of −5-0° C. The reaction was completed as detected by TLC. After the reaction mixture was filtered, the filter cake was rinsed with ethylene glycol dimethyl ether (2.0 L×2) and well drained. The mother liquor was collected and added to a 50 L reactor and cooled to −6° C. An aqueous solution of sodium borohydride (863.85 g/9 L of water, 22.835 mol) was slowly added dropwise over about 4.5 h at a controlled temperature of −10-0° C., with heat and a large amount of gas released. The mixture was stirred for 16 h at a controlled temperature of −5-0° C. The reaction was completed as detected by TLC. The solution of citric acid (500.00 g) in water (5.0 L) was slowly added dropwise to the reactor to quench the reaction, with a large amount of gas released. When almost no gas was released, the mixture was adjusted to pH=4-5 with citric acid (5500.00 g) and extracted with ethyl acetate (10.0 L×2), followed by liquid separation. The organic phases were combined, washed with brine (5.0 L×2), dried over anhydrous sodium sulfate (1500.00 g), and filtered. The mother liquor was collected and concentrated by rotary evaporation under a reduced pressure of −0.095 MPa at 50° C. to evaporate the solvent to obtain a crude product as a white solid (2467.00 g). To a 10 L reactor was added n-heptane (3.0 L), followed by the above crude product (2467.00 g). The mixture was slurried at room temperature for 2 h and filtered. The filter cake was collected. The filter cake was dried under a reduced pressure of −0.095 MPa at 50° C. to obtain compound 3 as a white solid (1562.30 g, 66.16% yield).

$^1$H NMR (400 MHz, CHLOROFORM-d) δ 4.64 (br s, 1H), 3.80-3.92 (m, 1H), 3.51 (br d, J=7.09 Hz, 2H), 2.17 (br s, 1H), 1.48 (s, 9H), 0.96 (s, 9H).

Step 3: Compound 4

To a 50 L reactor was added dichloromethane (12.0 L) at room temperature, followed by imidazole (1957.78 g, 28.757 mol) and triethylamine (1818.71 g, 17.973 mol) with stirring. The mixture was cooled to −40° C. Thionyl chloride (1026.37 g, 8.627 mol) was slowly added dropwise over about 1 h at a controlled temperature T=−40 to −20° C., with heat released. Compound 3 (1562.30 g, 7.189 mol) was dissolved in dichloromethane (4.0 L). The resulting solution was added dropwise over 1 h at a controlled temperature of −30 to −20° C. The mixture was stirred for 2 h at a controlled temperature of −30 to −20° C., then slowly warmed to room temperature and allowed to react for another 14 h. The reaction was completed as detected by TLC. The reaction was quenched with water (6.0 L) at room temperature and extracted with dichloromethane (2.0 L×2). The organic layer was washed with brine (4.0 L), dried over anhydrous sodium sulfate (1.0 kg), and filtered. The mother liquor was collected and concentrated by rotary evaporation under a reduced pressure of −0.090 MPa at 40° C. to obtain a residue as an oil (1860.00 g). To a 50 L reactor were added acetonitrile (3.0 L) and water (10.0 L), followed by ruthenium trichloride monohydrate (3.24 g, 0.014 mol) and sodium periodate (1845.26 g, 8.627 mol). The mixture was well mixed by stirring and cooled to 8° C. The above oil (1860.0 g) was dissolved in acetonitrile (7.0 L). The resulting solution was slowly added dropwise to the reactor over about 1 h at a controlled temperature of 5-15° C., with heat released. After 2 h, the reaction was completed as detected by TLC. The reaction mixture was filtered through celite, and the filter cake was washed with ethyl acetate (10.0 L). The mother liquor was collected and subjected to liquid separation to separate out the upper organic layer, which was then stirred in a 10% aqueous solution of sodium thiosulfate (10.0 L) for 0.5 h, followed by liquid separation. The organic phase was washed with saturated brine (10.0 L×8), followed by extraction. The organic phase was dried over anhydrous sodium sulfate (1000.0 g) and filtered. The mother liquor was collected and concentrated by rotary evaporation under a reduced pressure of −0.095 MPa at 50° C. to obtain a crude product as an off-white solid (1322.0 g). To a 10 L reactor were added n-heptane (2520.0 mL) and ethyl acetate (72.0 mL), followed by the above crude product (1322.0 g). The mixture was slurried at room temperature for 2 h and filtered. The filter cake was rinsed with n-heptane (1.0 L), drained well, collected, and dried under a reduced pressure of −0.095 MPa at 50° C. to obtain compound 4 as an off-white solid (1234.00, 61.49% yield).

$^1$H NMR (400 MHz, CHLOROFORM-d) δ 4.49-4.55 (m, 1H), 4.40-4.44 (m, 1H), 4.10 (d, J=6.15 Hz, 1H), 1.49 (s, 9H), 0.94 (s, 9H).

Example 2: Preparation of Compound 6

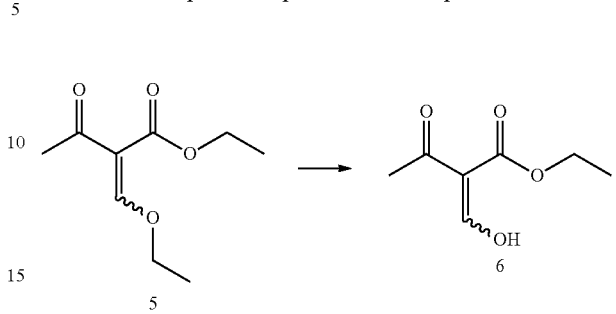

To a 50 L reactor was added water (20.0 L) at room temperature, followed by compound 5 (4025.94 g, 21.634 mol). The mixture was stirred for 4 h at a controlled temperature of 26-35° C. The reaction was completed as detected by HPLC. The reaction mixture was left standing, and the lower organic phase was separated out. The upper aqueous phase was extracted with methyl tert-butyl ether (4.0 L×2), followed by liquid separation. The organic phases were pooled, washed with saturated brine (4.0 L), dried over anhydrous sodium sulfate (1500.00 g), and filtered. The mother liquor was collected and concentrated by rotary evaporation under a reduced pressure of −0.095 MPa at 45° C. to remove the solvent to obtain compound 6 as a pale yellow liquid (3230.13 g, 93.89% yield, 99.397% purity).

$^1$H NMR (400 MHz, CHLOROFORM-d) δ=9.21 (d, J=6.0 Hz, 1H), 4.27 (q, J=7.2 Hz, 2H), 2.56 (s, 3H), 1.34 (t, J=7.2 Hz, 3H).

Example 3: Preparation of Compound 13

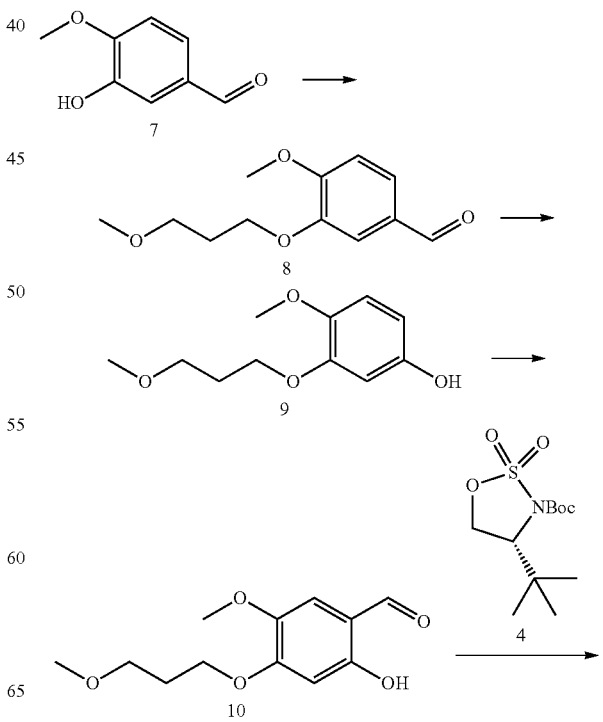

-continued

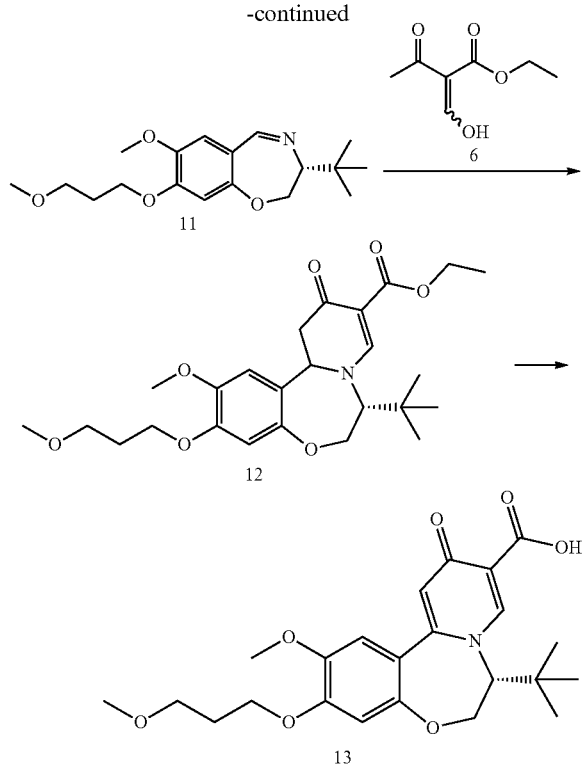

Step 1: Compound 8

To a 50 L reactor were added anhydrous ethanol (20.0 L) and water (10.0 L) at room temperature, followed by compound 7 (5000.00 g, 32.226 mol), potassium carbonate (4946.65 g, 35.450 mol) and 1-bromo-3-methoxypropane (5601.50 g, 35.450 mol). The mixture was well mixed by stirring. The mixture was heated to 75-85° C. and refluxed for 16 h. The reaction was completed as detected by HPLC. The reaction mixture was concentrated by rotary evaporation under a reduced pressure of −0.095 MPa at 50° C. to evaporate a mixture of ethanol and water (22.0 L). The concentrate was diluted with water (15.0 L) and extracted with ethyl acetate (15.0 L) and seperated. The organic layer was washed with brine (10.0 L), dried over anhydrous sodium sulfate (2.0 kg) and filtered. The mother liquor was collected and concentrated by rotary evaporation under a reduced pressure of −0.095 MPa at 50° C. to obtain compound 8 as a brown oil (7373.15 g, 97.43% yield, 97.378% purity).

$^1$H NMR (400 MHz, CHLOROFORM-d) δ 9.76-9.94 (m, 1H), 7.42-7.48 (m, 2H), 6.98 (d, J=8.03 Hz, 1H), 4.18 (t, J=6.53 Hz, 2H), 3.95 (s, 3H), 3.57 (t, J=6.09 Hz, 2H), 3.33-3.39 (m, 3H), 2.13 (quin, J=6.34 Hz, 2H).

Step 2: Compound 9

To a 50 L reactor was added dichloromethane (17.0 L) at room temperature, followed by 80% m-CPBA (4786.69 g, 22.265 mol) with stirring. The mixture was well mixed by stirring without dissolution. The solution of compound 8 (3660.12 g, 15.904 mol) in dichloromethane (4.0 L) was added dropwise to the reactor over about 2.5 h at a controlled temperature T=30-40° C., with heat released. The mixture was stirred at 40° C. for 15 h. The reaction was completed as detected by HPLC. The reaction mixture was cooled to room temperature and filtered. After being well drained, the filter cake was rinsed with dichloromethane (5.0 L×2). The filtrate was collected and washed 2 times under stirring with 10% sodium bicarbonate (7.0 L×2) and 10% sodium bisulfite (13.3 L×2), followed by liquid separation (the aqueous phase was tested for oxide residue with potassium iodide starch test paper). The organic phases were pooled and washed with brine (12.0 L), followed by liquid separation to collect the organic phase. The organic phase was concentrated by rotary evaporation under a reduced pressure of −0.090 MPa at 40° C. to obtain a black oil (4.06 kg). The oil was dissolved in methanol (10.5 L), and 2 M potassium hydroxide (10.5 L) was added. The mixture was stirred for 1 h at a controlled temperature of 30-40° C. The reaction was completed as detected by HPLC. The reaction mixture was concentrated by rotary evaporation under a reduced pressure of −0.095 MPa at 50° C. to evaporate a mixture of methanol and water (10.0 L). The concentrate was diluted with water (3.5 L) and extracted with isopropyl acetate (3.5 L×2), followed by liquid separation. The aqueous layer was kept and washed with 4 M potassium hydroxide (5.0 L). The aqueous phases were pooled. The pH was adjusted to 4-5 by slowly adding 37% hydrochloric acid (2.5 L) dropwise at a controlled temperature of 20-30° C. Ethyl acetate (5.0 L×2) was added for extraction. The organic phases were pooled and washed with brine (7.0 L), followed by liquid separation. The organic phase was dried over anhydrous sodium sulfate (2.5 kg) and filtered. The mother liquor was collected and concentrated under a reduced pressure of −0.090 MPa at 40° C. to obtain compound 9 as a brown oil (2780.13 g, 79.20% yield, 96.101% purity).

$^1$H NMR (400 MHz, CHLOROFORM-d) δ 6.75 (d, J=8.53 Hz, 1H), 6.49 (d, J=2.89 Hz, 1H), 6.36 (dd, J=2.82, 8.60 Hz, 1H), 4.07 (t, J=6.40 Hz, 2H), 3.82 (s, 3H), 3.60 (t, J=6.15 Hz, 2H), 3.38 (s, 3H), 2.06-2.14 (m, 2H).

Step 3: Compound 10

To a 50 L reactor were sequentially added tetrahydrofuran (18.0 L), magnesium chloride (2397.00 g, 25.176 mol) and triethylamine (2397.00 g, 25.176 mol) at room temperature. Compound 9 (2780.13 g, 12.588 mol) was dissolved in tetrahydrofuran (3.0 L), and the resulting solution was added to the reactor, followed by paraformaldehyde (1133.92 g, 12.588 mol). The mixture was heated to 65-70° C. and refluxed for 16 h. The reaction was completed as detected by HPLC. The reaction mixture was cooled to room temperature, adjusted to pH=3-4 by slowly adding 2 M hydrochloric acid (17.0 L) dropwise at a controlled temperature of 20-30° C. and extracted with ethyl acetate (9.0 L×2), followed by liquid separation. The organic phases were combined, washed with brine (6.0 L×2), dried over anhydrous sodium sulfate (2.0 kg), and filtered. The mother liquor was collected and evaporated by rotary evaporation under a reduced pressure of −0.095 MPa at 50° C. to obtain a residue as a black oil (2847.12 g), which was then slurried with ethanol (1.5 L×3) and filtered. The filter cake was rinsed with ethanol (0.5 L), well drained, and collected. The filter cake was dried under a reduced pressure of −0.095 MPa at 50° C. to obtain compound 10 as a off-white solid (1712.03 g, 56.67% yield, 99.334% purity).

$^1$H NMR (400 MHz, CHLOROFORM-d) δ 11.29 (s, 1H), 9.55-9.67 (m, 1H), 6.83 (s, 1H), 6.42 (s, 1H), 4.10 (t, J=6.48 Hz, 2H), 3.79 (s, 3H), 3.49 (t, J=6.05 Hz, 2H), 3.28 (s, 3H), 2.06 (quin, J=6.27 Hz, 2H).

Step 4: Compound 11

To a 50 L reactor were sequentially added anhydrous ethanol (20.0 L), 2000.02 g of compound 11 (2000.02 g, 8.163 mol), anhydrous potassium carbonate (1707.16 g, 12.245 mol) and compound 4 (2987.58 g, 10.612 mol) at room temperature. The mixture was well mixed by stirring with partial dissolution. The mixture was warmed to 65-75°

C. and allowed to react for 15 h with the temperature maintained. The reaction was terminated when completed as detected by HPLC. When the mixture was cooled to 20-40° C., 37% hydrochloric acid (6587.2 mL) was slowly added dropwise at a controlled temperature of 20-40° C., with a large amount of gas generated and heat released in the early stage. The mixture was stirred at a controlled temperature of 30-40° C. for 16 h. The mixture was cooled to 20-30° C. The mixture was adjusted to pH=9-10 by adding dropwise 14.5 L of a 4 M solution of sodium hydroxide at a controlled temperature of 20-40° C., with heat released. The reaction mixture was transferred out and concentrated by rotary evaporation under a reduced pressure of −0.090 MPa at 50° C. to evaporate a mixture of ethanol and water (20.5 L). The residue was extracted with n-heptane (20.0 L×2), stirred for 0.5 h, and left standing for liquid separation. The organic phases were combined and washed with brine (5.0 L×6), followed by liquid separation. The organic phase was dried over anhydrous sodium sulfate (2.0 kg) and filtered. The mother liquor was collected and concentrated by rotary evaporation under a reduced pressure of −0.090 MPa at 50° C. until a constant weight was reached to obtain a residue as a yellow oil (2570.05 g, 90.889% purity).

To a dry 10 L reactor was added 3600.0 mL of n-heptane at room temperature, followed by the above residue (2570.05 g). Stirring was started. When the mixture was warmed to 40° C., the crude product was uniformly dispersed and completely dissolved. Cooling was started. The mixture was slowly cooled to 8° C. within 2 h, with a yellow solid precipitated. The crystallization was allowed at a maintained temperature of 0-10° C. for 2 h, with a large amount of a yellow solid precipitated. The mixture was poured out for suction filtration. After being well drained, the filter cake was transferred to a 3 L single-necked flask and subjected to rotary evaporation with an oil pump under a reduced pressure of −0.095 MPa at a controlled bath temperature of 20-30° C. to remove the solvent until a constant weight was reached to obtain compound 11 as a yellow solid (1856.04 g, 62.20% yield, 93.750% purity).

$^1$H NMR (400 MHz, CHLOROFORM-d) δ 10.31 (s, 1H), 7.34 (s, 1H), 6.57 (s, 1H), 4.18-4.26 (m, 3H), 4.07 (dd, J=5.33, 9.60 Hz, 1H), 3.88 (s, 4H), 3.60 (t, J=5.96 Hz, 2H), 3.39 (s, 3H), 2.17 (quin, J=6.21 Hz, 2H), 1.47 (s, 9H), 1.06 (s, 9H).

Step 5: Compound 12

To a dry 50 L reactor were sequentially added ethylene glycol dimethyl ether (14.2 L), compound 11 (2845.22 g, 8.261 mol), compound 6 (2659.63 g, 16.522 mol) and glacial acetic acid (996.87 g, 16.522 mol) at room temperature. The mixture was well mixed by stirring with complete dissolution. The mixture was warmed to 75-85° C. and allowed to react for 16 h with the temperature maintained. The reaction was terminated when completed as detected by HPLC. The reaction mixture was cooled to 20-30° C. and diluted with ethyl acetate (8.0 L). The reaction was quenched by slowly adding a 10% solution of sodium carbonate (5.6 L×3), with a small amount of gas released at the early stage. The mixture was stirred for 10 min and left standing for liquid separation. The lower aqueous phase was separated out, and the upper organic phase was kept. The organic phase was washed with 10% sodium chloride solution (5.6 L×2) and left standing for liquid separation. The organic phase was kept, dried over anhydrous sodium sulfate (2.0 kg), and filtered. The mother liquor was collected and concentrated by rotary evaporation under a reduced pressure of −0.090 MPa at 50° C. to evaporate the solvent until a constant weight was reached to obtain compound 12 as a reddish-brown oil (4559.00 g, 84.48% yield, 70.650% purity).

$^1$H NMR (400 MHz, CHLOROFORM-d) δ 8.40 (s, 1H), 6.80 (s, 1H), 6.51 (s, 1H), 4.30 (br d, J=12.35 Hz, 1H), 4.04-4.11 (m, 3H), 3.79 (s, 3H), 3.49 (t, J=5.99 Hz, 2H), 3.36 (br d, J=2.93 Hz, 1H), 3.28 (s, 3H), 2.06 (quin, J=6.24 Hz, 2H), 1.02 (s, 9H).

Step 6: Compound 13

To a dry 50 L reactor was added tetrahydrofuran (5.4 L) at room temperature, and stirring was started. Compound 12 (2081.45 g, 3.188 mol) was dissolved in tetrahydrofuran (5.0 L), and the resulting solution was added to the reactor with complete dissolution. Then iodine (1618.28 g, 6.376 mol) and dimethyl sulfoxide (994.78 g, 12.752 mol) were sequentially added. The system was well mixed by stirring and had a reddish-brown color. The mixture was warmed to 65-75° C. and allowed to react for 16 h with the temperature maintained. The reaction was terminated when completed as detected by HPLC. The mixture was cooled to 20-40° C., and a 4 M solution of sodium hydroxide (6.5 L) was added dropwise at a controlled temperature of 20-40° C., with heat released. After the dropwise addition, the mixture was allowed to react for 2 h, with the temperature maintained at 30-40° C. The reaction was terminated when the intermediate was completely reacted as detected by TLC. A 10% solution of sodium sulfite (7.34 L) was added to the reactor to quench the excess iodine, with no heat released. The mixture was stirred for 0.5 h. The mixture was adjusted to pH=5-6 by dropwise adding 4 M hydrochloric acid (4.3 L) at a controlled temperature of 20-40° C., with heat released. Ethyl acetate (5.8 L×3) was added to the reactor for extraction. The mixture was left standing for liquid separation. The upper organic phase was kept, washed with brine (5.6 L×3), and left standing for liquid separation. The lower aqueous phase was separated out, and the upper organic phase was kept, dried over anhydrous sodium sulfate (2.0 kg), and filtered. The mother liquor was collected. The mother liquor was concentrated by rotary evaporation under a reduced pressure of −0.090 MPa at 50° C. to evaporate the solvent until a constant weight was reached to obtain a residue as a brown solid (1558.00 g).

To a 50 L reactor were added absolute ethanol (17.0 L) and the above combined crude product (3402.00 g) at room temperature. The mixture was slurried and stirred at 25-35° C. for 17 h and discharged for filtration. After being well drained, the filter cake was rinsed with absolute ethanol (1.0 L×2) and collected. The filter cake was subjected to rotary evaporation under a reduced pressure of −0.095 MPa at 50° C. to remove the solvent until a constant weight was reached to obtain a pale yellow solid (1892.13 g).

To a 50 L reactor were added absolute ethanol (9.5 L) and the above pale yellow solid (1892.13 g) at room temperature. The mixture was well mixed by stirring without dissolution. Warming was started. When the reactor was warmed to 68° C., the solid was completely dissolved. The mixture was stirred for 5 min. At a reactor temperature of 71° C., activated carbon (190.00 g) was added. The mixture was stirred at a controlled temperature of 70-75° C. for 0.5 h and filter while hot. After being well drained, the filter cake was rinsed with absolute ethanol (250.0 mL×2). The mother liquor was collected and added to a 50 L reactor. Warming was started. When the mixture was warmed to 68° C., complete dissolution was achieved. The mixture was stirred for 15 min. When the reactor temperature reached 74° C., slow cooling was started. When the reactor temperature was reduced to 62° C. after 1 h of cooling, a large amount of a white solid was precipitated. The cooling was continued, with a decrease of 10° C. per hour, for a total of 3 h. When the reactor temperature was reduced to 45° C., the cooling was continued until a room temperature of 31° C. was reached. The crystallization was allowed for 15 h with the temperature maintained. At a reactor temperature of 28° C., the mixture was discharged for filtration. After being well drained, the filter cake was rinsed with absolute ethanol (1.0 L×2), well drained, and collected. The filter cake was added to a 50 L reactor, followed by deionized water (10.0 L). The mixture was stirred and slurried at a room temperature of 25-35° C. for 2.5 h. The mixture was discharged for filtration. After well drained, the filter cake was rinsed with deionized water (1.0 L), well drained, collected, and dried in a vacuum drying oven under a reduced pressure of −0.095 MPa at 50° C. for 42 h to obtain compound 13 as a pale yellow solid (1621.11 g, 54.10% yield, 99.880% purity).

$^1$H NMR (400 MHz, CHLOROFORM-d) δ 15.72 (br s, 1H), 8.32-8.93 (m, 1H), 6.60-6.93 (m, 2H), 6.51 (br s, 1H), 4.38-4.63 (m, 2H), 4.11 (br dd, J=4.52, 12.23 Hz, 3H), 3.79-3.87 (m, 3H), 3.46-3.54 (m, 2H), 3.29 (s, 3H), 2.07 (quin, J=6.24 Hz, 2H), 0.77-1.21 (m, 9H).

What is claimed is:

1. A preparation method for a compound of formula (I),

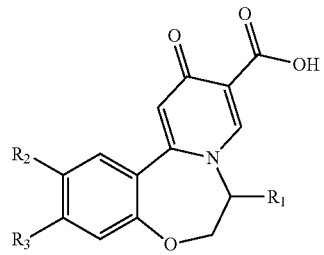

(I)

comprising the following steps:

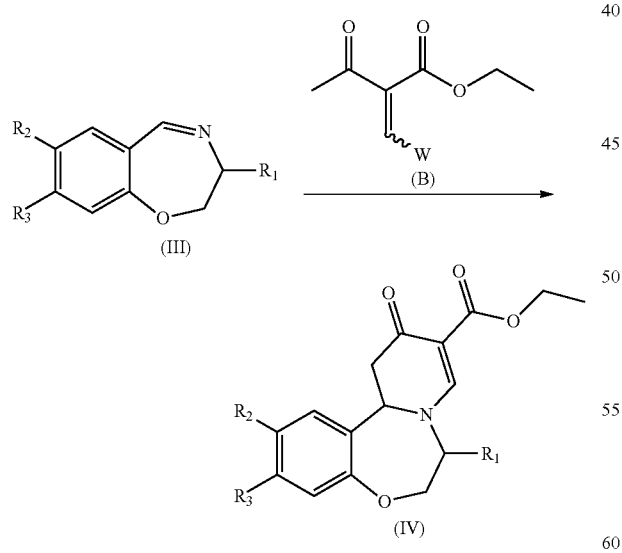

wherein,

W is selected from OH, $C_{1-6}$ alkoxy and $C_{1-6}$ alkylamino;

$R_1$ is selected from $C_{1-6}$ alkyl;

$R_2$ is selected from H, F, Cl, Br, I, CN, $C_{1-6}$ alkyl, $C_{1-6}$ alkoxy, $C_{1-6}$ alkylamino, —C(=O)—$C_{1-6}$ alkyl, $C_{3-6}$ cycloalkyl and 3-6 membered heterocycloalkyl, wherein the $C_{1-6}$ alkyl, $C_{1-6}$ alkoxy, $C_{1-6}$ alkylamino, $C_{3-6}$ cycloalkyl and 3-6 membered heterocycloalkyl are optionally substituted with 1, 2 or 3 $R_a$;

$R_3$ is selected from

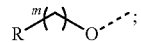

R is selected from OH, CN, NH$_2$, $C_{1-6}$ alkoxy, $C_{1-6}$ alkylamino, $C_{1-6}$ alkylthio, —C(=O)—$C_{1-6}$ alkyl, —C(=O)—$C_{1-6}$ alkylamino, —O—C(=O)—$C_{1-6}$ alkylamino, —NH—C(=O)—$C_{1-6}$ alkoxy, $C_{2-5}$ alkenyl, $C_{2-5}$ heteroalkenyl, $C_{3-6}$ cycloalkyl and 3-6 membered heterocycloalkyl, wherein the $C_{1-6}$ alkyl, $C_{1-6}$ alkoxy, $C_{1-6}$ alkylamino, $C_{1-6}$ alkylthio, —C(=O)—$C_{1-6}$ alkyl, —C(=O)—$C_{1-6}$ alkylamino, —O—C(=O)—$C_{1-6}$ alkylamino, —NH—C(=O)—$C_{1-6}$ alkoxy, $C_{2-5}$ alkenyl, $C_{2-5}$ heteroalkenyl, $C_{3-6}$ cycloalkyl and 3-6 membered heterocycloalkyl are optionally substituted with 1, 2 or 3 $R_b$;

m is selected from 0, 1, 2, 3, 4 and 5;

$R_a$ and $R_b$ are each independently selected from COOH, F, Cl, Br, I, OH, CN, NH$_2$, CH$_3$, CH$_2$CH$_3$, CH$_2$CH$_2$CH$_3$, OCH$_3$, —NHCH$_3$, —N(CH$_3$)$_2$ and CF$_3$.

2. The preparation method according to claim 1, wherein R is selected from OH, CN, NH$_2$, $C_{1-3}$ alkoxy, $C_{1-3}$ alkylamino, $C_{1-3}$ alkylthio, —C(=O)—$C_{1-3}$ alkyl, —C(=O)—$C_{1-3}$ alkylamino, —O—C(=O)—$C_{1-3}$ alkylamino, —NH—C(=O)—$C_{1-3}$ alkoxy, $C_{2-3}$ alkenyl, $C_{2-3}$ heteroalkenyl, $C_{3-6}$ cycloalkyl and 3-6 membered heterocycloalkyl, wherein the $C_{1-3}$ alkyl, $C_{1-3}$ alkoxy, $C_{1-3}$ alkylamino, $C_{1-3}$ alkylthio, —C(=O)—$C_{1-3}$ alkyl, —C(=O)—$C_{1-3}$ alkylamino, —O—C(=O)—$C_{1-3}$ alkylamino, —NH—C(=O)—$C_{1-3}$ alkoxy, $C_{2-3}$ alkenyl, $C_{2-3}$ heteroalkenyl, $C_3$-cycloalkyl and 3-6 membered heterocycloalkyl are optionally substituted with 1, 2 or 3 $R_b$.

3. The preparation method according to claim 2, wherein R is selected from OH, CN, NH$_2$,

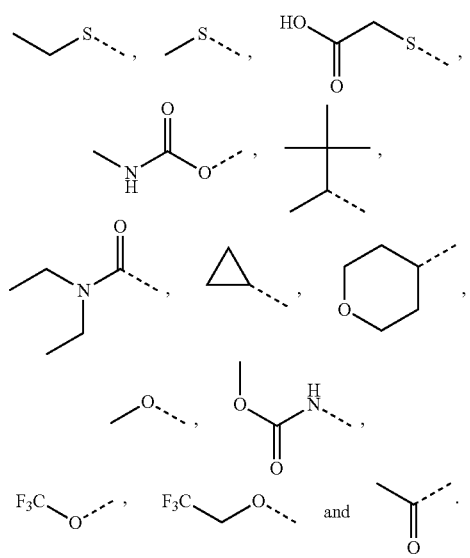

4. The preparation method according to claim 1, wherein W is selected from OH, —OCH$_2$CH$_3$ and —N(CH$_3$)$_2$.

5. The preparation method according to claim 1, wherein $R_1$ is selected from

6. The preparation method according to claim 1, wherein $R_2$ is selected from H, F, Cl, Br, I, CN, $C_{1-3}$ alkyl, $C_{1-3}$ alkoxy, $C_{1-3}$ alkylamino, —C(=O)—$C_{1-3}$ alkyl, $C_{3-6}$ cycloalkyl and 3-6 membered heterocycloalkyl, wherein the $C_{1-3}$ alkyl, $C_{1-3}$ alkoxy, $C_{1-3}$ alkylamino, —C(=O)—$C_{1-3}$ alkyl, $C_{3-6}$ cycloalkyl and 3-6 membered heterocycloalkyl are optionally substituted with 1, 2 or 3 $R_a$.

7. The preparation method according to claim 6, wherein $R_2$ is selected from Cl, Br, CN, $CH_3$,

8. The preparation method according to claim 1, wherein $R_3$ is selected from

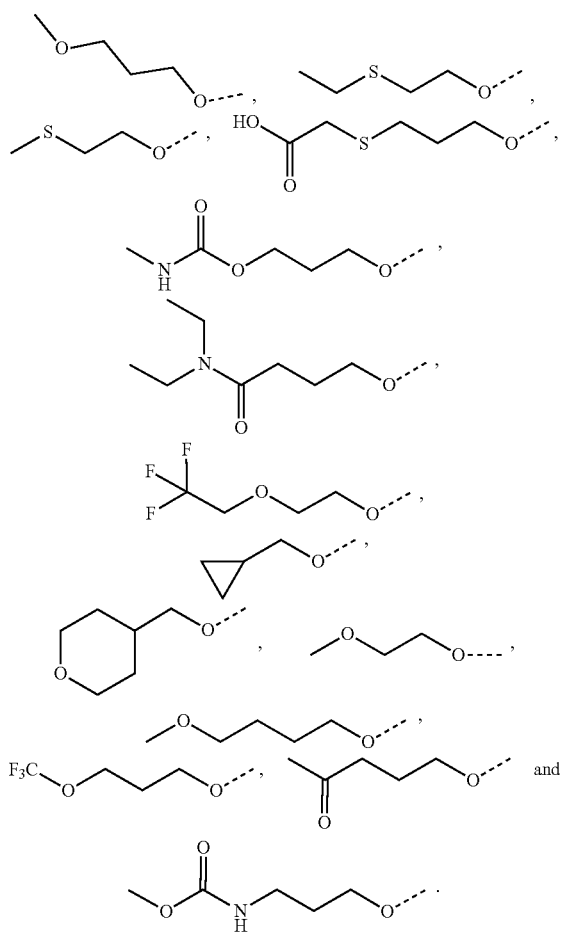

9. The preparation method according to claim 1, comprising the following step:

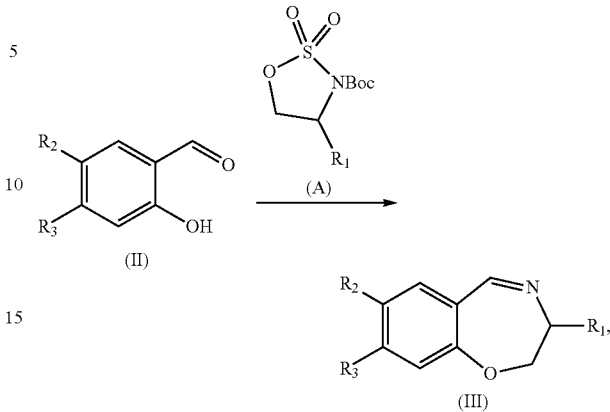

wherein $R_1$, $R_2$ an $R_3$ are previously defined.

10. The preparation method according to claim 9, comprising the following steps:

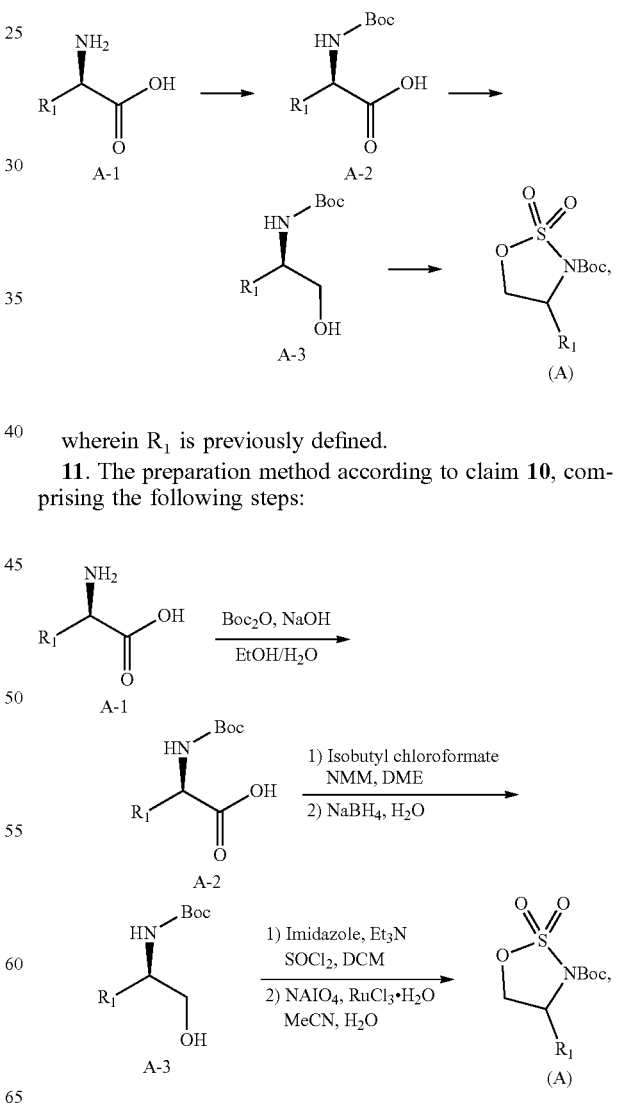

wherein $R_1$ is previously defined.

11. The preparation method according to claim 10, comprising the following steps:

wherein $R_1$ is previously defined.

12. The preparation method according to claim 1, comprising the following steps:
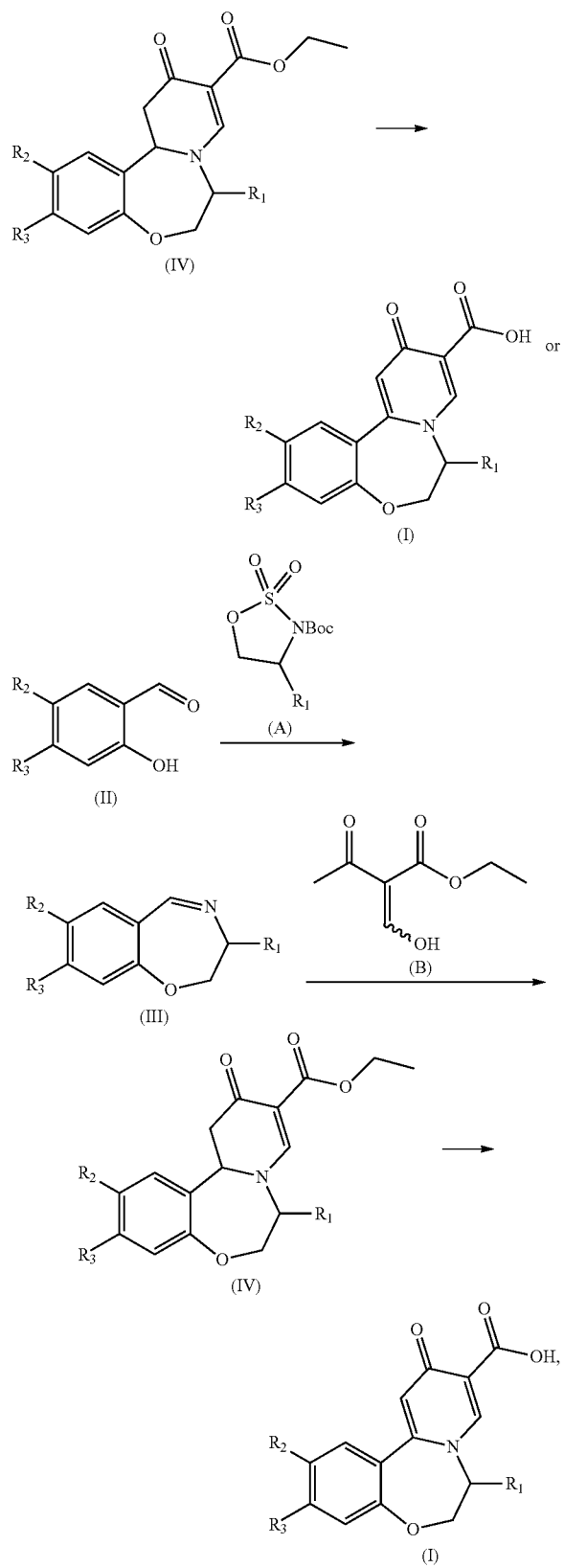
wherein $R_1$, $R_2$ and $R_3$ are previously defined.
13. A preparation method for compound 13,
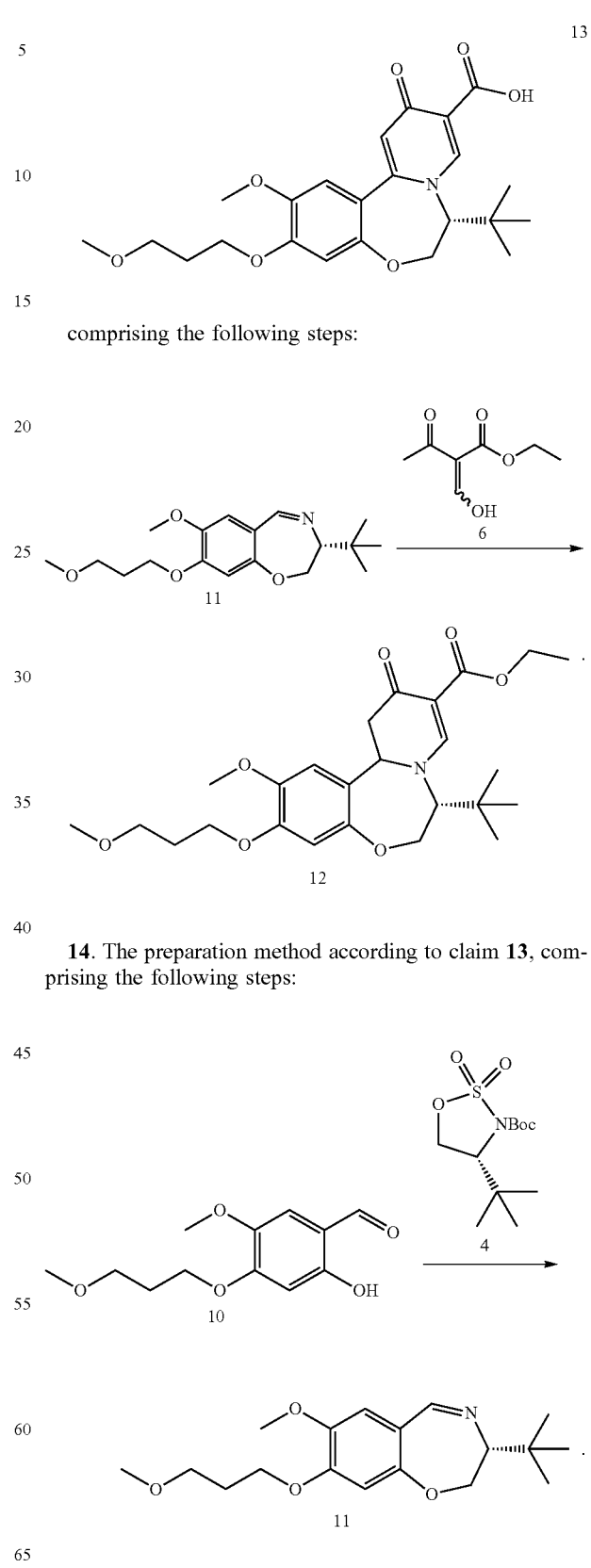
comprising the following steps:
14. The preparation method according to claim 13, comprising the following steps:

15. The preparation method according to claim 14, comprising the following steps:
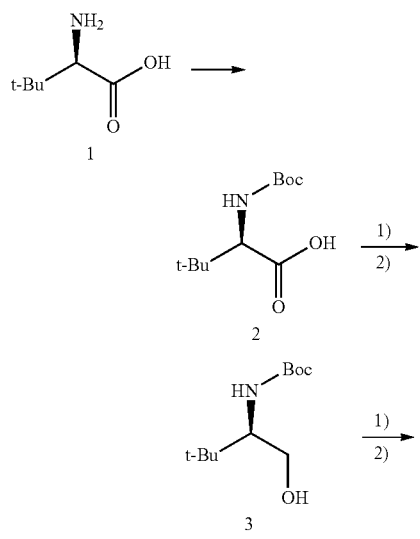
16. The preparation method according to claim 15, comprising the following steps:
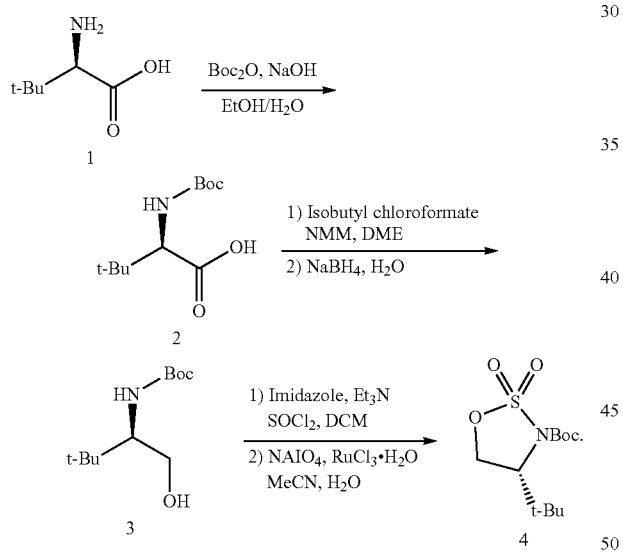
17. The preparation method according to claim 13, comprising the following steps:
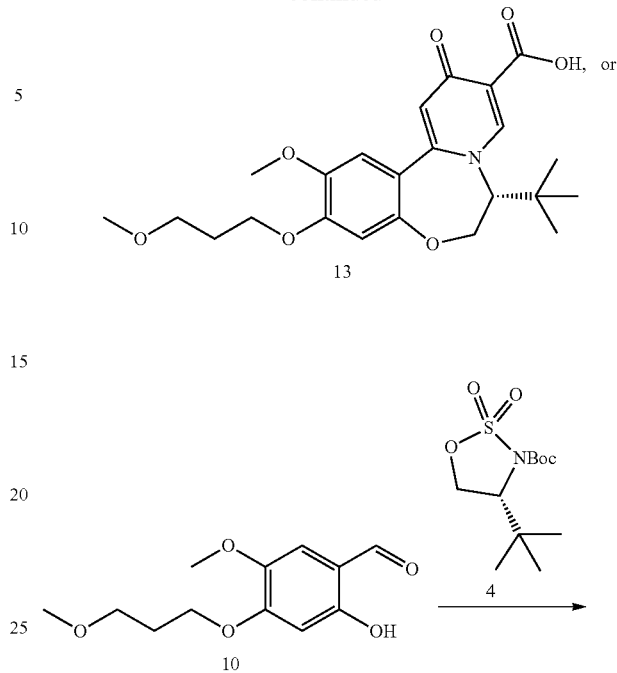
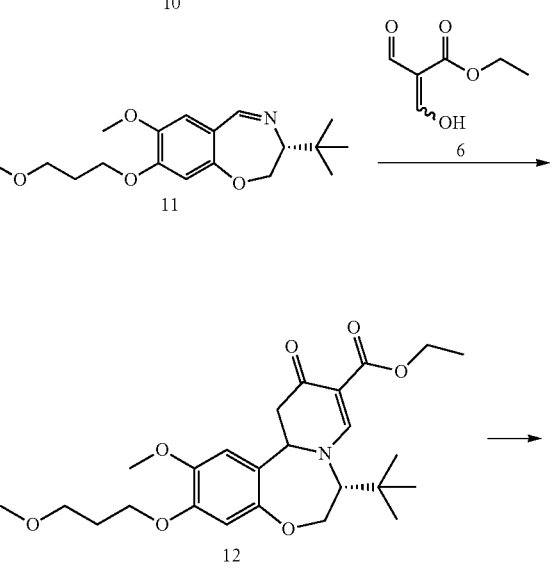
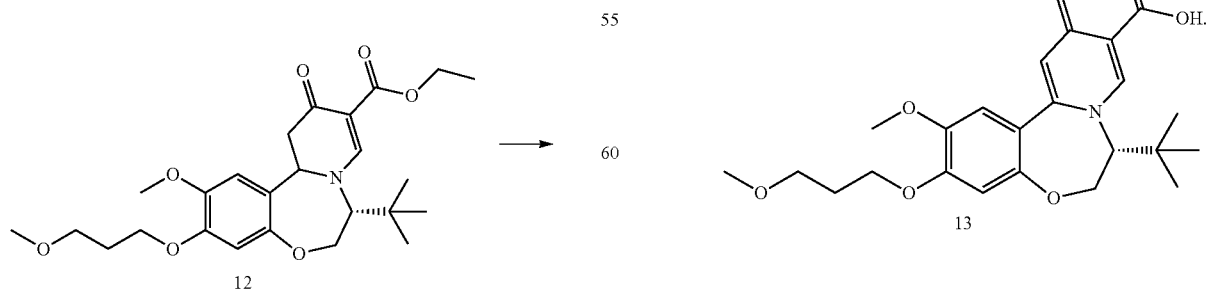
* * * * *